United States Patent [19]
Broad

[11] Patent Number: 5,776,675
[45] Date of Patent: Jul. 7, 1998

[54] IDENTIFICATION OF COMPOUNDS MODULATING PROTEIN/CELL MEMBRANE ASSOCIATION

[75] Inventor: Peter Michael Broad, Congleton, United Kingdom

[73] Assignee: Zeneca Limited, London, United Kingdom

[21] Appl. No.: 446,856

[22] PCT Filed: Dec. 14, 1993

[86] PCT No.: PCT/GB93/02543

§ 371 Date: Jun. 5, 1995

§ 102(e) Date: Jun. 5, 1995

[87] PCT Pub. No.: WO94/13818

PCT Pub. Date: Jun. 23, 1994

[30] Foreign Application Priority Data

Dec. 14, 1992 [GB] United Kingdom ............... 9226065

[51] Int. Cl.[6] .................. C12Q 1/68; C12N 1/19; C12N 15/79; C07K 14/00
[52] U.S. Cl. .............. 435/6; 435/254.21; 435/320.1; 435/325; 530/350
[58] Field of Search .............. 435/6, 172.3, 320.1, 435/254.21, 325; 935/23, 27; 536/23.1, 23.4, 23.5, 23.7; 530/350

[56] References Cited

U.S. PATENT DOCUMENTS 5,202,456   4/1993   Rando .................................. 558/438

FOREIGN PATENT DOCUMENTS

| 0 123 811 B1 | 11/1984 | European Pat. Off. . |
| 496027 | 7/1992 | European Pat. Off. . |
| WO 89/05816 | 6/1989 | WIPO . |
| 90 14422 | 11/1990 | WIPO . |
| 91 13155 | 9/1991 | WIPO . |
| WO 93/10246 | 5/1993 | WIPO . |
| 93 24630 | 12/1993 | WIPO . |

OTHER PUBLICATIONS

Kamata et al. (1991) Myristylation alters DNA–binding activity and transactivation of FBR (gag-fos protein. Mol. Cell. Biol. 11:765–772, Feb. 1991.

Hancock et al., "A CAAX or a CAAL motif and a second signal are sufficient for plasma membrane targeting of ras proteins", *The EMBO Journal*, vol. 10, No. 13, 1991, pp. 4033–3039.

Kamata et al., "Myristylation Alters DNA–Binding Activity and Transactivation of FBR (gag–fos) Protein", *Molecular and Cellular Biology*, Feb. 1991, pp. 765–772.

Kamata et al., "Inhibitory Effect of Myristylation on Transrepression by FBR (Gag–Fos) Protein", *Molecular and Cellular Biology*, Feb. 1992, pp. 876–882.

Quilliam et al., "Membrane–targeting potentiates guanine nucleotide exchange factor CDC25 and SOS1 activation of Ras transforming activity", *Proc. Natl. Acad. Sci.*, vol. 91, Aug. 1994, pp. 8512–8516.

Migeon et al., "Regulation of cAMP–mediated Gene Transcription by Wild Type and Mutated G–protein α Subunits", *The Journal of Biological Chemistry*, vol. 269, No. 46, 1994, pp. 29146–29152.

Badia et al., "Membrane Targeting of Firefly Luciferase: A New Bioluminescent Reporter Gene", *Analytical Biochemistry*, vol. 217, 1994, pp. 333–335.

Ravanello, et al: "An NH2–terminal peptide from the vaccinia virus L1R protein directs the myristylation and virion envelope localization of a heterologous fusion protein", Journal of Biological Chemistry, vol. 268, No. 10, Apr. 5, 1993, pp. 7585–7593. see the whole document.

Pellman, et al: "An N–terminal peptide from p60src can direct myristylation and plasma membrane localization when fused to heterologous proteins", Nature, vol. 314, Mar. 1985, pp. 374–377. see the whole document.

Resh, et al: "Identification of a 32K plasma membrane protein that binds to the myristylated amino–terminal sequence of p60v–scr", Nature, vol. 346, Jul. 5, 1990, pp. 84–86. see the whole document.

Shoji et al. (1990) Biochem. Biophys. Res. Comm. 173:894–901, Dec. 31, 1990.

*Primary Examiner*—George C. Elliott
*Assistant Examiner*—Robert Schwartzman
*Attorney, Agent, or Firm*—Cushman Darby & Cushman Intellectual Property Group of Pillsbury Madison & Sutro, LLP

[57] ABSTRACT

A method for identifying compounds which modulate protein/cell membrane association which method comprises contacting a test compound with a cell, having (i) a cell membrane, (ii) a heterologous protein comprising a reporter sequence and a recognition sequence for cell membrane association, (iii) a reporter system which is acted upon by the reporter sequence such that there is a measurable change in cell phenotype upon modulation of protein/cell membrane association by the test compound, and detecting any change in cell phenotype.

15 Claims, 4 Drawing Sheets

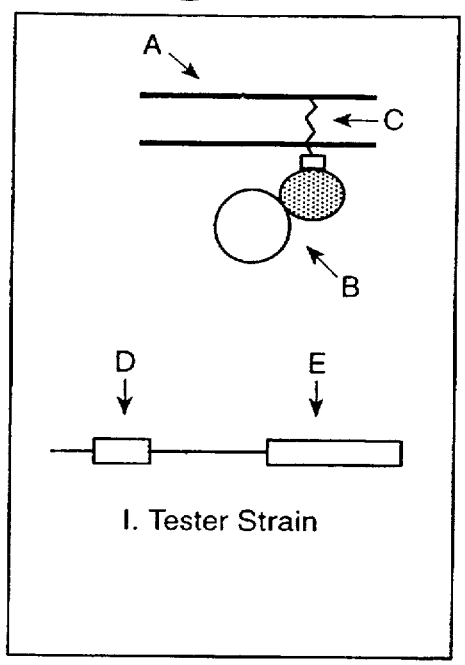
Fig. 1A
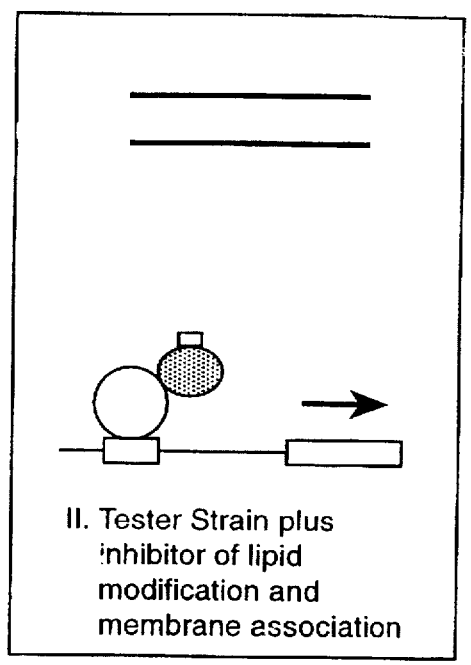
Fig. 1B
Fig. 2A
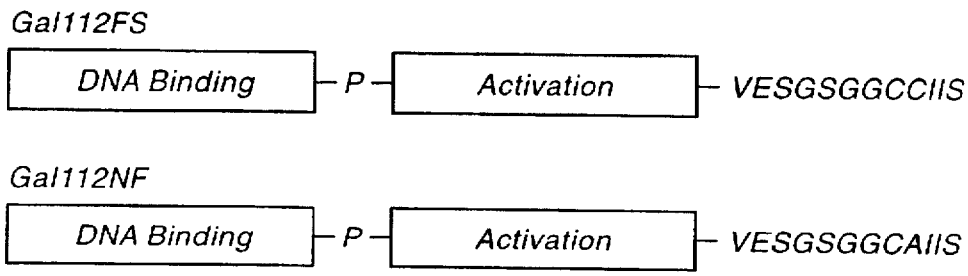
Fig. 2B
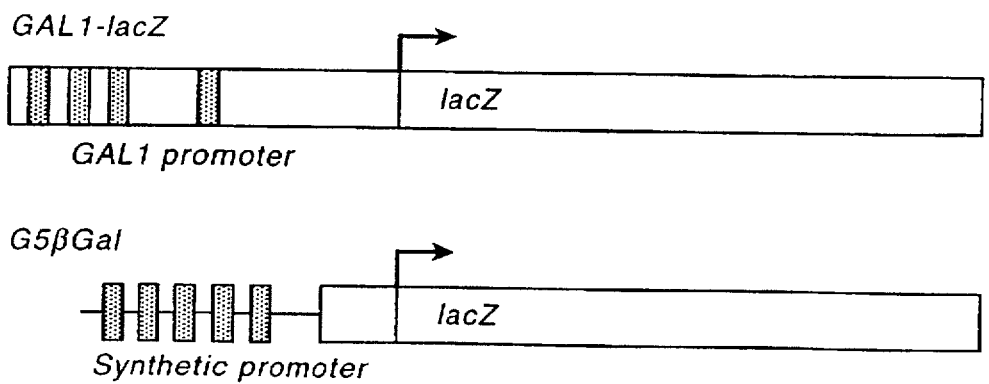

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GCCCGGGGTC GACACTAGTT AACTAG 26

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

ACGACGGGCC CCAGCTGTGA TCAATTGATC GCCGG 35

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TCGACGGATC CGAGCT 16

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ATCTGGTTCT GGTGGTTGTT GTATTATTTC TTAAG 35

( 2 ) INFORMATION FOR SEQ ID NO:5:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

ACGTTAGACC AAGACCACCA ACAACATAAT AAAGAATTCA GCT 43

( 2 ) INFORMATION FOR SEQ ID NO:6:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

ACGTTAGACC AAGACCACCA ACACGATAAT AAAGAATTCA GCT           43

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

ATCTGGTTCT GGTGGTTGTG CTATTATTTC TTAAG           35

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CCATGCTTAA GCGCCAAGC           19

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

ATACCCTCTA GAGTCGAC           18

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

Val Glu Ser Gly Ser Gly Gly Cys Cys Ile Ile Ser
 1             5                   10

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:11:

Val Glu Ser Gly Ser Gly Gly Cys Ala Ile Ile Ser
 1             5                   10

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

Ser Gly Ser Gly Gly Cys Cys Ile Ile Ser
1               5                   10

IDENTIFICATION OF COMPOUNDS MODULATING PROTEIN/CELL MEMBRANE ASSOCIATION

This application is a 371 of PCT/GB93/02543, filed Dec. 14, 1993.

The present invention relates to a method for identifying compounds which modulate protein/cell membrane association. The method provides an in vivo assay for inhibitors of protein/cell membrane association wherein modulation of the association leads to a detectable change in cell phenotype. The invention also relates to heterologous proteins, nucleic acid sequences encoding these, corresponding DNA constructs, and recombinant cells, all for use in the above method.

Numerous proteins are modified by the covalent addition of lipids (1). The hydrophobic side-chains the proteins in selected cellular membranes. We refer to this process as membrane association. Inhibition of membrane association of certain lipid-modified proteins is a potential target for therapeutic intervention, since membrane association is usually critical for full biological activity of these proteins. By way of example, inhibition of the membrane association of ras proteins has been proposed as a method for the selective inhibition of oncogenic forms ras (2). Additionally the activity of oncogenic src variants is dependent upon their membrane association through N-myristoylation (3).

Current procedures for identifying inhibitors of lipid modification and membrane association involve screening compounds, such as peptides, against purified samples of individual enzymes involved in the lipid modification process (8). This is time-consuming and expensive since it involves the purification and perhaps cloning of these enzymes. Furthermore, not all steps involved in the membrane association process may be amenable to study in this way. For example, the proposed interaction of lipid-modified proteins with membrane components (9) may be difficult to reproduce in vitro. An alternative approach was reported by Finegold et al (10). Activation of the pheromone response pathway of *Saccharomyces cerevisiae* (*S. cerevisiae*) leads to growth arrest. The activity of the pheromone response pathway is dependent upon the integrity of the g subunit of the pheromone receptor-associated G protein. This subunit is isoprenylated. Thus, inhibition of isoprenylation reverses growth arrest in a *S. cerevisiae* strain in which the pheromone response pathway is active. This provides a growth/no growth assay or inhibitors of isoprenylation. However, this assay is not specific to isoprenylation, since compounds inhibiting the pheromone response pathway at any point will be active.

It has been reported elsewhere that amino acid sequences around the site of lipid modification in some proteins act as membrane association signals (5,6). Hancock et al (5) have demonstrated that fusion of ras membrane association signals to protein A relocates protein A to the inner surface of the plasmamembrane. Similarily Pellman et al (6) showed that fusion of β-globin to a src membrane association signal relocated that fusion to the plasmamembrane. In both cases neither of the fusions conferred a readily measurable phenotype on the cell and the location of the fusion protein could only be determined by time-consuming an labour intensive immunological methods.

We now provide an in vivo assay or inhibitors of protein/cell membrane association wherein modulation of association leads to a detectable change in cell phenotype.

In a first aspect of the present invention we provide a method for identifying compounds which modulate protein/cell membrane association which method comprises contacting a test compound with a cell, having (i) a cell membrane, (ii) a heterologous protein comprising a reporter sequence and a recognition sequence for cell membrane association, (iii) a reporter system which is acted upon by the reporter sequence such that there is a measurable change in cell phenotype upon modulation of protein/cell membrane association by the test compound, and detecting any change in cell phenotype.

The method may be used to identify inhibitors or enhancers of any biological process which leads directly or indirectly to modulation of protein/cell membrane association. A particular advantage of the method is that it enables compounds to be screened for their ability to inhibit membrane association without the need to clone or purify any of the enzymatic species involved in membrane association. The method will detect, in addition to direct inhibitors of membrane association, inhibitors of any lipid modification process and inhibitors of lipid biosynthesis. The method may be used in screens, such as rapid throughput screens, for compounds which are potential inhibitors/enhancers of biochemical processes resulting in modulation of protein/cell membrane association. Such screens may for example involve large collections of chemical compounds, natural products and/or broths. Alternatively such screens may involve intracellularly expressed protein libraries. Since active compounds confer a gain in function (activation of the reporter system) upon a test cell, the method is very sensitive; a small level of reporter activity is easily observed if the background is zero.

Any convenient cell may be used where modulation of protein/cell membrane association such as lipid modification or membrane insertion can be linked via a reporter system to a phenotypic change. Examples of convenient cells include yeasts such as *S. cerevisiae, Schizosaccharomyces pombe, Kluvermyces lactis* and *Pichia pastoris,* bacteria such as *Escherischia coli,* plant cells such as tobacco and maize, and animal cells. We include cells which naturally contain the machinery required for membrane association of proteins, and cells where such machinery has been introduced, for example by genetic engineering, and cells where the natural machinery has been altered by addition, alteration (for example by mutation) replacement or deletion of some component.

The invention also relates to a cell for use in the above method and having (i) a cell membrane, (ii) a heterologous protein comprising a reporter sequence and a recognition sequence for cell membrane association, (iii) a reporter system which is acted upon by the reporter sequence such that there is a measurable change in cell phenotype upon modulation or protein/cell membrane association by a test compound.

The cell membrane used in the above method may be any convenient intracellular cell membrane, including the nuclear membrane, organelle membranes and the plasmamembrane. The membrane with which the heterologous fusion protein is associated need not be the same membrane to which proteins which naturally contain the membrane association signal are targeted; the presence of other signals in the fusion protein may alter the targeting. For example, the presence of a nuclear localisation signal in combination with a membrane localisation signal may locate the fusion protein to the nuclear membrane, whereas in the absence of the nuclear lccalisation signal the protein would be localised to other cell membranes.

The heterologous protein used in the above method comprises a reporter sequence and a recognition sequence for cell membrane association. It conveniently comprises a fusion of the reporter sequence and the recognition sequence. The reporter sequence is conveniently a transcriptional activator and preferably comprises a DNA binding domain and a transcription activation domain. The DNA binding domain may be substituted for by a protein domain that interacts with a protein already bound to a promoter; in either case the function of this part of the protein is to enable the protein to bind to a specific promoter when the fusion protein is not membrane-associated. Such transcriptional activator/recognition sequence fusions can confer a simple phenotype on cells containing an appropriate reporter gene in that the gene is inactive when the activator is membrane-associated; but when that membrane association is inhibited the activator fusion can move to the reporter gene, bind to its promoter, and activate transcription of the reporter. In essence, the membrane association signal enables the activator to be sequestered away from the reporter gene. The above heterologous proteins together with nucleic acid sequences encoding these, form further and independent aspects of the invention.

The transcriptional activator conveniently comprises a DNA binding domain from a eukaryotic protein such as GAL4, or a prokaryotic protein such as the repressor protein LexA. These DNA binding domains are well characterised and known to be capable of tolerating fusion a variety, of activation domains (21, and refs. therein). Other DNA binding domains, such as the zinc binding domains, homeodomains, and basic domains (see ref. 23) may also be used in this method. The transcriptional activation domain may be natural or synthetic. Suitable activation domains of the 'acidic' class are described by Ptashne (ref. 21) these acidic domains have the useful property of being able to function in many eukaryotic species. It may be convenient for the transcriptional activator to contain a nuclear localisation signal. The activator must be able to tolerate fusion chimaeric signals without destroying these functions.

The membrane association signal may, for example be a signal for farnesylation, geranylgeranylation, palmitoylation, myristylation or some other lipid modification. Additionally the signal may be a novel sequence created, for example from of all or part of two or more different signals. The heterologous protein containing the membrane association signal is encoded on an expression construct. This construct contains a promoter to drive expression of the fusion protein together with appropriate nucleic acid sequences to allow efficient RNA processing and translation of the mRNA. The promoter may be constitutive or regulated.

The reporter system conveniently comprises a promoter/reporter gene acted on by a transcriptional activator as described above. The promoter of the reporter gene will contain binding for the transcriptional activator and is preferably essentially inactive in the absence of bound activator, thus maximising the response upon modulation of membrane association. The promoter may be a naturally occurring DNA sequence, or it may be a synthetic sequence, or it may be a combination of the two. A number of factors will influence the difference between the inactive and active states of the reporter gene. These include the affinity of the transcriptional activator for its binding sites in the promoter, the number of those binding sites, and strength of the activation domain of the activator. The reporter gene conveniently confers an readily measurable phenotyne upon the cell. The reporter gene may conveniently comprise the coding sequence of a enzyme such as $E.\ coli$ β-galactosidase, firefly luciferase, or choramphenicol acetyl transferase, in which the phenotype conferred is an enzyme activity which may easily be measured, often by use of a colour chance. Alternatively the reporter gene may be a gene essential for the growth of the cell, for example a gene encoding an essential metabolic enzyme. In this case, activation of the gene will allow cell growth. Alternatively the reporter gene may encode an enzyme which metabolises a toxic substrate. In the presence of this substrate, activation of the reporter gene will again allow growth of the cell. Examples of other convenient promoter/reporter gene combinations will be apparent to the person of ordinary skill.

If required the reporter system may incorporate an amplification step. By way of example, the transcriptional activator released from membrane association activates transcription of a gene encoding another transcription factor, preferably one comprising a strong transcriptional activation domain and a different DNA binding specificity. This second transcription factor then activates transcription of a reporter gene such as those described above. The effect of an inhibitory agent on membrane association can, in this way, be amplified into a larger response from a reporter system.

The invention also relates to DNA constructs which enable the heterologous protein comprising a reporter sequence and a recognition sequence for cell membrane association optionally together with the reporter system to be introduced/transfected into the host cell. The DNA constructs contain sequences to allow maintenance of the constructs as episomal plasmids, or to enable integration of he constructs into the genome of the host cell. The constructs will, in general, also be shuttle vectors which can be propagated in $E.\ coli$ to allow the generation of sufficient quantities of material.

In a further aspect of the invention at least two distinct fusion protein/reporter gene systems are introduced into the same cell. This allows simultaneous screening for the ability of compounds to modulate either or both of the relevant processes. In such a polyfunctional assay, distinct reporter genes and promoters are conveniently used.

The method of the invention is particularly applicable to lipid-modified proteins which are anchored to intracellular membranes and to the inner face of the plasmamembrane. It therefore encompasses such modifications as palmitcylation, isoprenylation and N-myristoylation but is not directly applicable to, for example, glycolipid modificatons which anchor proteins to the extracellular face of the plasmamembrane.

N-myristoylation is the cotranslational addition of myristate to the amino terminal glycine residue of selected proteins (3). These proteins include the α subunit of some heterotrimeric G proteins, cAMP-dependent protein kinase, src, myristoylated protein kinase C substrate (MARCKS) protein and numerous retroviral coat proteins. The sequence motif which confers N-myristoylation is localised to the first ten amino acids of the protein. It has been demonstrated that an N terminal peptide from p60src can direct myristoylation and plasmamembrane association when fused to heterologous proteins (6). Considerable conservation of the N-myristoylation machinery has occurred in evolution, such that the human N-myristoyl transferase, which shares 44% homology with the $S.\ cerevisiae$ enzyme, will complement a deficiency the yeast enzyme (7).

Isoprenylation may be conveniently subdivided into three types (reviewed ref. 4)

(1) Farnesylation. This is the attachment of farnesyl (15 carton chain) groups to cysteine residues near the carboxy terminus of proteins. The target sequence for farnesylation is CAAX (where C is cysteine, A is an aliphatic amino acid, and X, the C-terminal residue, is any amino acid except leucine. Following attachment of the farnesyl group to the cysteine residue of this sequence, target proteins are further modified by a proteolytic cleavage which removes the last three residues, and methylation of the new carboxy terminus. Additionally, palmitoylation of cysteines close to the farnesylated cysteine occurs in some proteins. Farnesylated proteins include g subunits of some heterotrimeric G proteins, ras proteins, and the nuclear lamins. The farnesyl group is donated by farnesyl pyrophosphate, an intermediate on the sterol biosynthetic pathway. The enzymology of farnesylation and its associated modifications appears to have been conserved in eukaryotes. These processes occur in both mammalian cells and in the budding yeast *S. cerevisiae*.

Of particular interest are the ras proteins. Recently, the sequence requirements for stable plasmamembrane association of ras proteins have been determined (5). In addition to the carboxy terminal tetrapeptide which signals farnesylation, an adjacent sequence is required. In c-Ha-ras, this adjacent sequence includes a cysteine which becomes palmitoylated subsequent to the initial farnesylation. For c-Ki-ras, the adjacent sequence contains a set of positively charged amino acids which, though they do not become modified, are necessary for membrane association. It has been demonstrated that it possible to fuse the last eleven amino acids of a ras protein to a cytosolic protein and confer membrane association upon that protein (5). Thus this region of ras proteins defines a signal for membrane association.

(2) Geranylgeranylation at CAAL sequences. The addition of geranylgeranyl (C-20chain) groups to the cysteine residues of proteins terminating in CAAX, where X is leucine, is very similar to farnesylation. As with farnesylation, proteolytic cleavage and methylation steps follow the initial modification. The enzyme which performs this type of geranylgeranylation is geranylgeranyl transferase I. This enzyme contains a subunit which is common to farnesyl transferase. Proteins which undergo this modification include several ras-related G proteins such as rac1, rac2 and ra1A and the g subunits of some heterotrimeric G proteins. The similarity of this form of geranylgeranylation to farnesylation suggests that the carboxy terminal regions of these proteins will, like the comparable regions of ras proteins, constitute distinct membrane association signals capable of tolerating fusion to heterologous proteins.

(3) Geranylgeranylation at CC and CAC sequences. Geranylgeranylation of cysteine residues in these carboxy terminal sequences is mediated by a different enzyme from that above. Furthermore, the signal for geranylgeranylation appears to be distributed throughout the target protein (see ref. 24). Thus, for this particular form of isoprenylation, there may not be a distinct membrane association sequence which can be transferred to a heterologous protein.

The method of the present invention is conveniently used to find inhibitors of farnesylation-dependent and geranylgeranylation-dependent membrane association. In addition to direct inhibition of these processes, it will be apparent from FIG. 4 that inhibitors of sterol biosynthetic pathway, such as inhibitors of HMG-CoA reductase, will inhibit these membrane association processes by depleting the substrates used in these reactions. Inhibitors of sterol biosynthesis have application in the management of cholesterol levels. Inhibitors of farnesylation are potential antitumour agents against tumours containing an oncogenic form of a ras gene and may have application in modulating signalling pathways involving farnesylated Gg proteins. Inhibitors of geranylgeranylation may have application as modulating signalling pathways mediated by geranylgeranylated Gg proteins. Inhibitors of myristoylation have potential application as modulators of signal transduction pathways dpendent upon a myristoylated Gα protein, as inhibitors of src mediated cell transformation and as inhibitors of retroviral coat assembly. Inhibitors of membrane association processes may also be sytotoxic agents.

In another aspect of the present invention we provide a method for identifying membrane association signals. We have shown that membrane association can be used to confer a simple phenotype upon a cell. This phenotype can be used to screen libraries of peptide sequences to find those which function as membrane association signals. In another aspect of the invention, we provide a method to generate mutations in membrane association processes. Mutagenesis of a cell containing the heterologous protein/reporter gene system may generate mutants in which the fusion protein can no longer be localised to the membrane. These mutants may be distinguished by the change in cell phenotype consequent upon reporter gene activation.

Compounds which modulate protein/cell membrane association can act as reporter gene inducers. In a further feature of the invention we use this to provide cells where inhibitors of protein/cell membrane association are used to switch on genes of interest.

Therefore in a further aspect of the invention we provide a cell, having (i) a cell membrane, (ii) a heterologous protein comprising a transcripton activator and a recognition sequence for cell membrane association, (iii) a promoter/gene transcription system which is acted upon by the transcription activator such that gene transcription is activated by a compound which inhibits association of the heterologous protein and the cell membrane.

In this aspect of the invention the gene which is transcribed is conveniently a gene which is used for some other purpose other than to monitor the membrane attachment of the activator. For example the gene may encode a protein whose production in high quantities is desirable but the constant expression of which is detrimental to the cell. Multicellular organisms such as plants or animals may be engineered to contain cells containing the components of this switch. Application of the inducing compound can then be used to induce expression of a desired gene in some or all of the cells of the organism. The applications of such a system are varied and include for example controlling the fertility and yield of crop plants and, in animal cells, inducing the expression of heterologous proteins or increasing the levels of endogenously expressed proteins. Additionally, if the expressed gene encodes for example a toxin gene, the system can be used to ablate certain cells at a desired time. The use of a tissue-specific promoter, or some other form of regulated promoter to drive expression of the fusion protein enables the inducible gene regulatory system to be established in a desired subset of cells.

The invention will now be illustrated but not limited by reference to the following Figures and Examples wherein:

BRIEF DESCRIPTION OF THE DRAWINGS

FIGS. 1A–1B illustrates the method of the invention. The double solid lines denoted by A represent a membrane. The protein denoted by B consists of; a DNA binding domain (open oval), a transcription activation domain (shaded oval) and a membrane association signal (open box). The zigzag denoted by C represents lipid moieties anchoring the protein to the membrane. The reporter gene is represented by D and E. D denotes binding sites for the transcriptional activator within the promoter of the gene. E denotes the coding region of the reporter gene.

Situation I represents the situation in the tester cell in the absence of any inhibitors of membrane association. The activator is lipid-modified and sequestered in a membrane. The reporter gene is therefore inactive since no activator is bound to he binding sites in the promoter.

Situation II represents the situation in the presence of an inhibitor of lipid modification. In the absence of lipid modifications the activator is not longer membrane-associated and is free to migrate to the reporter gene and bind to the promoter of that gene. This results in activation of reporter gene transcription, denoted by the larger arrow. The figure shows how inhibitors of membrane association which act directly or indirectly upon lipid modification may be detected. This system may be able to detect agents which inhibit membrane association by some mechanism other than inhibiting lipid modification; for example, if membrane association of a lipid-modified protein requires a specific interaction between that protein and a component of the target membrane, the inhibition of that interaction may be detectable.

FIG. 2A shows the structure of the GAL4based activators Gal112FS and Gal112NF. The DNA binding domain consists of amino acids 1-147 of GAL4 (ref. 17). The activation domain consists of amino acids 1-108 of the activation domain B112 (ref. 15). The C-terminal ten amino acid residues of Gal112FS are identical to the C-terminal ten amino acid residues (SEQ ID NO:10) of the S. cerevisiae RAS2 protein (ref. 18) The C-terminal ten amino acid residues (SEQ ID NO:11) of Gal112NF are identical to those of Gal112FS except for the exchange of an alanine for a cysteine four amino acids from the carboxy terminus. The primary structure of each activator consists of 268 amino acids. In the yeast expression vectors YCpGal112FS and YCpGal112NF the expression of each activator is driven by the S. cerevisiae ADH1 promoter. In the mammalian expression vectors pECE-FS and PECE-NF the expression of each activator is driven by the SV40 promoter/enhancer.

FIG. 2B shows the schematic structure of the reporter genes used in yeast and mammalian cells. Both are based on the E coli lacZ gene which encodes the enzyme β-galactosidase. The yeast reporter gene GAL1-lacZ is integrated into the S. cerevisiae genome. The promoter is the S. cerevisiae GAL1 promoter which contains four binding sites for GAL4 denoted by shaded boxes). The mammalian reporter gene G5βGal is supplied as a plasmid by transfection. The promoter is a synthetic promoter consisting of the human β-globin minimal promoter (open box) and 5 consensus GAL4 binding sites. The arrows above each construct indicate the start of transcription.

Figure 3A:
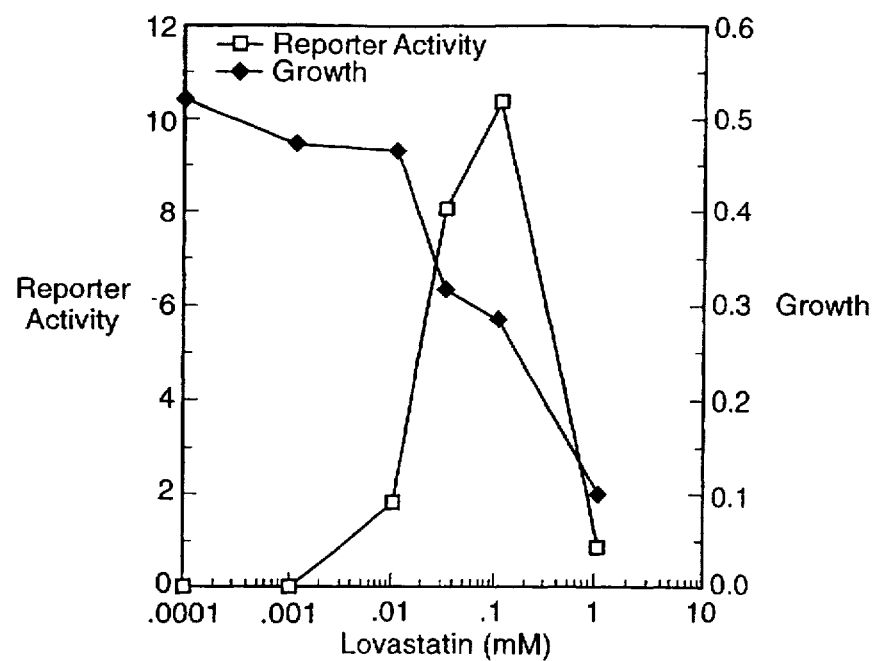

FIG. 3A shows a dose response of reporter gene activity in YT6::171 containing YCpGal112FS measured using ONPG as the substrate in the β-galactosidase assay. Yeast cultures were incubated overnight in the presence of various concentrations of lovastatin. Growth was measured as the increase in optical density at 595 nm over an 18 hour period in a microtitre plate. Reporter gene activity is the rate of increase in optical density at 420 nm after addition of reaction buffer OD change in 120 minutes) to the cultures. The figure shows that at intermediate concentrations of lovastatin, reporter gene transcripton is induced.

Figure 3B:
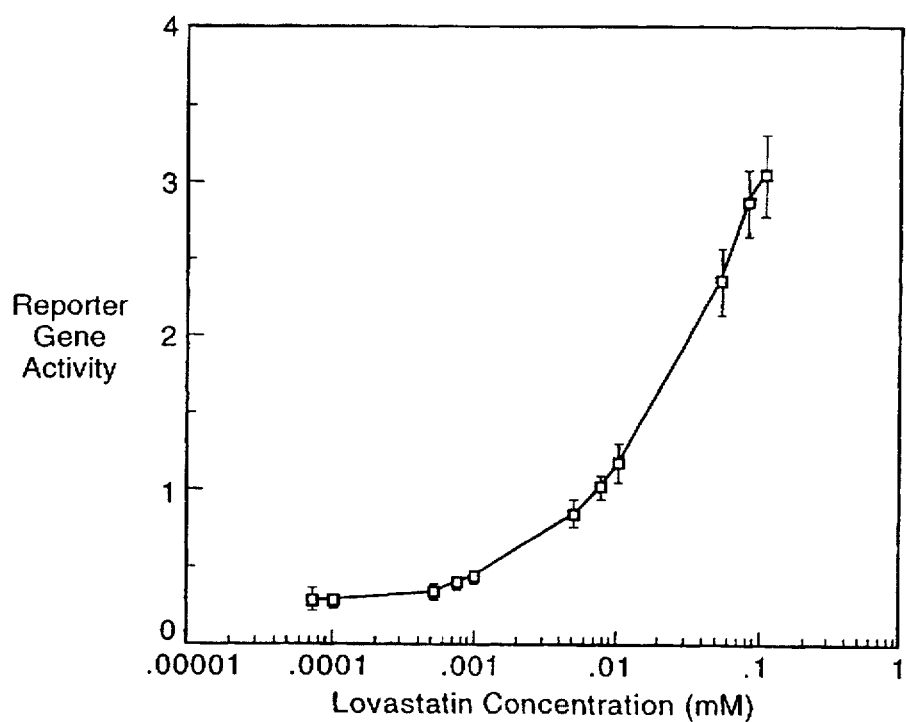

FIG. 3B shows a dose response of reporter gene activity in YT6::171 containing YCpGal112FS measured using CPRG as the substrate in the β-galactosidase assay. Activity is given as the change in absorbance at 570 nm over a period of 1 hour. Each point is the average of 20 readings; the error bars are standard deviations. The basal level of OD570 chance in the absence of lovastatin was 0.25 units.

Figure 4:
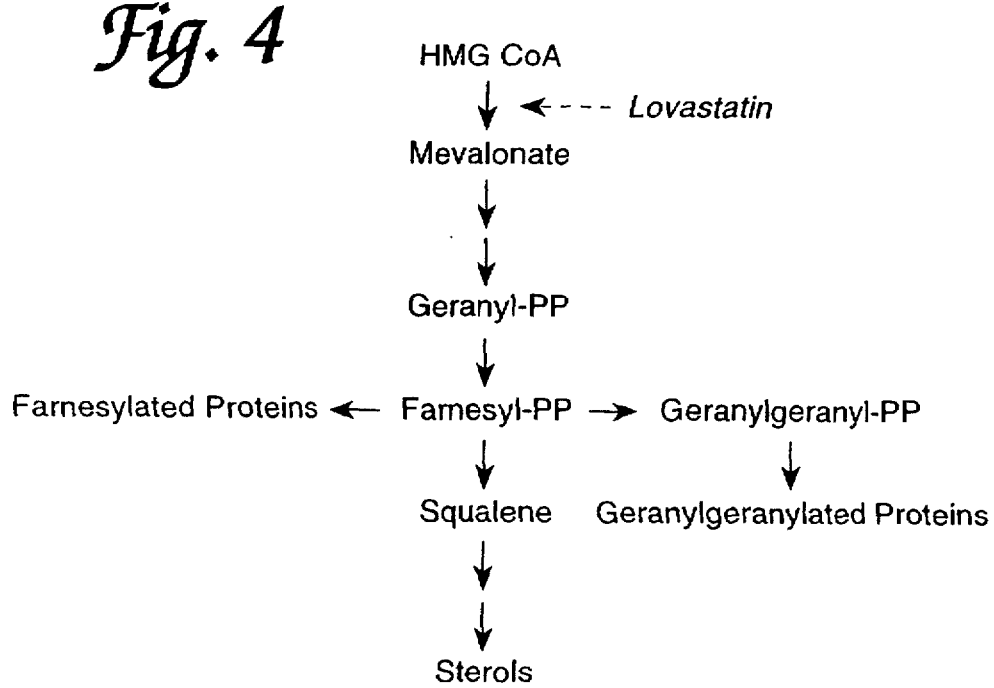

FIG. 4 outlines the biochemical pathway involved in sterol biosynthesis in eukaryotic cells. The substrates for geranylgeranylation and farnesylation of proteins are derived from the intermediate farnesyl pyrophosphate. Hence inhibition of this pathway the level of HMG-CoA reductase by agents such as lovastatin can lead to inhibition of protein modification. This can suppress the effects of activating mutations in ras (see ref. 16)

Figure 5:
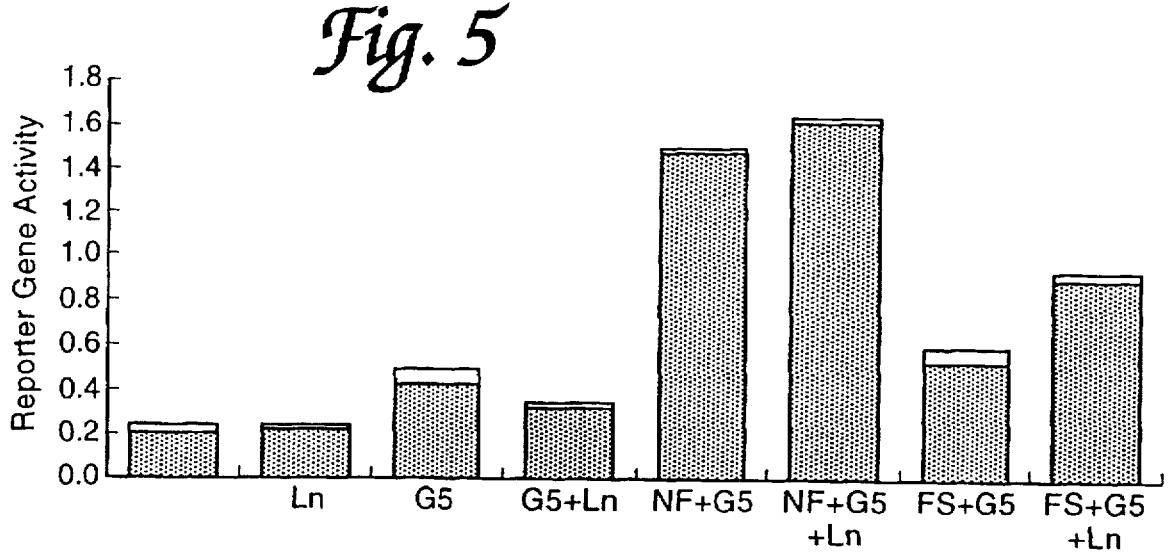

FIG. 5 shows the effect of lovastatin on reporter gene activity in COS-1 cells. Reporter gene activity was measured by the CPRG-based β-galactosidase assay. Lovastatin (1 µM) is abbreviated as ln. A set of transfections was performed using various combinations of the reporter plasmid pG5βGal labelled as G5the activator plasmids pECE-FS (labelled as FS) and pECE-NF (labelled as NF) and lovastatin (labelled as Ln). Lovatstatin was added at 1 µM to the indicated transfections. Each transfection was performed in duplicate; the shaded parts of the bars represent the averages of these duplicates and the unshaded parts of the bars represent the standard deviations. The vertical axis represents the change in OD 570 over 1.5 hours. The reaction was linear during this period, so these values are directly proportional to enzyme activity. The efficiency of the transfections, as measured by a growth hormone assay, as roughtly equal.

Figure 6:
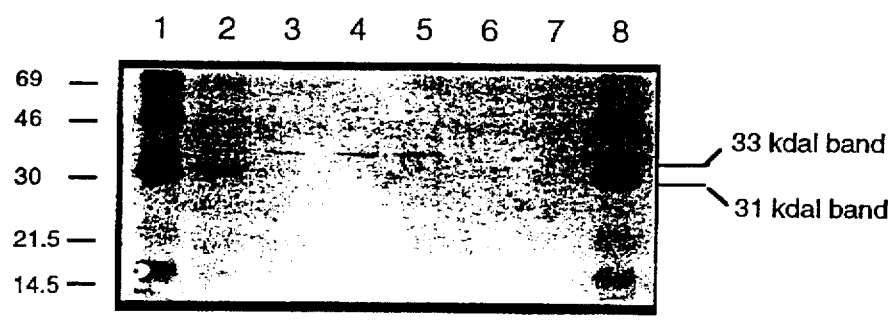

FIG. 6 shows a schematic representation of a Western blot of COS-1 cells transfected with activator constructs. The lanes are as follows:
1. 10 µl high molecular weight rainbow markers (from Amersham: molecular weights 14,3000–2000,000).
2. 25 µg total protein extract from COS-1 cells transfected with pECE-FS plus pRSVhGH.
3. 25 µg total protein extract from COS-1 cells transfected with pECE-NF plus pRSVhGH and incubated in the presence of 1 µM Lovastatin.
4. 25 µg total protein extract from COS-1 cells transfected with pECE-NF plus pRSVhGH.
5. 25 µg total protein extract from COS-1 cells transfected with pECE-NF plus pRSVhGH and grown in the presence by 1 µM Lovastatin.
6. 25 µg total protein extract from COS-1 cells transfected with pRSVhGH alone.
7. 25 µg total protein extract from COS-1 cells transfected with pRSVhGH alone and incubated in the presence of 1 µM Lovastatin.
8. 10 µl low molecular weight rainbow markers (from Amersham: molecular weights 2,350–46,000).

EXAMPLE 1

Inhibition of membrane association of a transcriptional activator in the yeast S. cerevisiae by the HMG-CoA reductase inhibitor, lovastatin In this example we show (i) that fusion of a membrane association signal to a transcriptional activator causes that protein to become inactive, presumably through lipid modification and consequent membrane association and (ii) that inhibition of -this presumed lipid modification renders the protein active again.

The yeast S. cerevisiae was used as a host organism. We used the E. coli β-galactosidase gene under control of the S. cerevisiae GAL1 promoter as a reporter gene. The GAL1 promoter contains binding sites for the transcriptional activator GAL4. Since GAL4 has been deleted from this strain, the reporter gene is inactive. We transformed plasmids expressing chimaeric GAL4based activators into this strain. We found that fusion of a membrane-association signal from a ras protein to the carboxy terminus of the activator resulted in inhibition of reporter gene activity, presumably due to farnesylation and membrane association of the activator. This inhibition could be reversed by the application of lovastatin, an HMG-CoA reductase inhibitor, which would be expected to inhibit farnesylation by inhibition of the sterol biosynthetic pathway.

Materials and methods

Yeast strains and plasmids

The host S. cerevisiae strain used was YT6::171 (11), which contains a GAL1-lacZ reporter gene integrated at the URA3 locus. The plasmid YCpGal112FS, which encodes a fusion protein consisting of the DNA binding domain of GAL4 (amino acids 1-147), the activation domain B112 and the last ten amino acids of the S. cerevisiae RAS2 protein, was constructed as follows: - The Hind III-EcoR I fragment from pSG424 (12) encoding GAL (1-147) was ligated into the Hind III and EcoR I sites of pBluescript SK+(Stratagene) to create pSK147. The polylinker of pSK147 was modified by replacing the sequence between the Pst I and Not I sites with the following annealed oligonucleotides: GCCCGGGGTCGACACTAGTTAACTAG (SEQ ID NO:1) and ACGACGGGCCCCAGCTGTGATCAAT-TGATGATCGCCGG (SEQ ID NO:2).This created the plasmid pSK147BX. The Hind III-Not I fragment of this plasmid was ligated into the Hind III-Not I fragment of the plasmid pADNS (13) to create pADGal147. The polylinker of the yeast single copy vector pRS315 (14) was replaced by cleaving the plasmid with Xho I and Sac I and inserting the following annealed oligonucleotides: TCGACGGATC-CGAGCT (SEQ ID NO:3) and GCCTAGGC. Into the bam HI site of the resultant plasmid, pRS315XS, the Bam HI fragment of pADGal147 was inserted such that the SacI site is 5' to the ADH1 promoter and the Kpn I site is 3'to the ADH1 terminator, creating the plasmid YCp15ADH147. A 320bp Eco RI fragment of plasmid pB112 (15) containing amino acids 1-108 of the acidic activation region 112 was ligated into the Eco RI site of pSK147 in the orientation maintaining the integrity of the reading frame to create pBXG112. The Hind III-Pst I fragment of pBXG112 was used to replace the Hind III- Pst I fragment of YCp15ADH147 to create YCp15G112. YCp15G112 is a centromeric expression plasmid which expresses the activator GAL(1-147)-B112 from the yeast ADh1 promoter. YCpGal112FS contains a membrane association signal. This was created by inserting the following annealed oligonucleotides between the Pst I and Sal I sites: ATCTGGTTCTG-GTGGTGGTTGTTGTATTATTTCTTAAG (SEQ ID NO:4) and ACGTTAGACCAAGACCACCAACAACAT-AATAAAGAATTCAGCT (SEQ ID NO:5) mutated membrane association signal created by inserting the following annealed oligonucleotides between the Pst I and Sal I sites: ATCTGGTTCTGGTGGTTGTGCTATTATTTCTTAAG (SEQ ID NO:7) and ACGTTAGACCAAGACCACCAA-CACGATAATAAAGAATTCAGCT (SEQ ID NO:6). Plasmids YCp15G112, YCpGal112FS and YCpGal112FS were transformed into YT6::171 by the lithium acetate method (19). Some of the clones obtained which contained YCpGal112FS exhibited instability. When they were restreaked and transferred to X-Gal indicator plates, these unstable clones gave rise to some blue colonies. Other clones were apparently stable since they gave rise only white colonies. One of the clones that gave only white colonies was picked and restreaked twice more to confirm that it was stable. This clone, designated clone 19, was used in β-galactosidase assays.

β-galactosidase assay

Yeast cells containing plasmids were grown in synthetic complete media lacking leucine. For reporter gene assays, stationary cultures were diluted 1:50 and crown overnight in 200 μl aliqouts in 96 well microtitre dishes. β-galactosidase activity was measured by a modification of the method of Ausabel et al (25) Equal volumes of 10×Z buffer and 4 mg/ml ONPG (o-Nitrophenyl-β-D-Galactopyranoside, from Sigma) in 1M phosphate pH7 were mixed. SDS was added to a final concentration of 0.1%. 50 μl of this cocktail was added to each well of the microtitre plate and the rate of appearance of product measured at 420 nm using a platereader. The optical density at 595 nm was taken as a measure of growth.

Similar experiments were performed using 10 mM CPRG (chlorophenolred-β-D-galactopyranoside, from Boehringer Mannheim) in place of 4 mg/ml ONPG. For this substrate, changes in optical density were measured at 570 nm.

Results and Discussion

YCpGal112FS expresses the protein shown in FIG. 2A–2B. This protein consists of a DNA binding domain which will bind to GAL4 sites, an activation domain, and the last ten residues of the yeast RAS2 protein (SGSGGCCIIS SEQ ID NO:12). By analogy with the experiments of Hancock et al (5), this carboxy terminal sequence from RAS2 should confer farnesylation, palmitoylation and membrane association upon the protein. In YT6::171 cells transformed with this construct there was a very low level of reporter gene activity Gal112 (15). Evidently the fusion of the carboxy terminal sequence of RAS2 inactivates the GAL4 fusion, presumably by causing it to become attached to a membrane so that it is unable to activate transcription of the reporter gene.

Inhibition of HMG-CoA reductase leads to inhibition of the sterol biosynthetic pathway and thus to the inhibition of formation of farnesyl pyrophosphate, the intermediate of this pathway used by farnesyl transferase. Application of lovastatin to mammalian cells leads to an accumulation of nonisoprenylated substrate proteins (20). Furthermore, lovastatin will revert the phenotype of activated ras mutations in Xenopus oocytes (16) and will rescue lethal yeast mutations dependent upon isoprenylation for their activity (10). We reasoned that if the inactivity of Gal112FS was due to farnesylation-dependent membrane association, then addition of lovastatin should lead to inhibition of farnesylation and membrane association of Gal112FS and consequently to activation of the reporter gene (see FIG. 4). Yeast cultures were incubated overnight in the presence of lovastatin (sodium salt, from Merck and Co.). We observed two effects of lovastatin upon YT6::171 containing YCpGal112FS (see FIG. 3A). Firstly, the lovastatin inhibited growth at concentrations of around 1 mM. This growth inhibition is attributable to cytotoxicity resulting from inhibition of sterol biosynthesis. Secondly, at lower concentrations of lovastatin, the predicted induction of reporter gene activity was observed. The optimum level for reporter gene stimulation was about 0.1 mM. The maximal level of induction of reporter gene was roughly equivalent to the level observed with the parental activator Gal112. Lovastatin had no effect on the reporter gene in the parental strain YT6::171; the reporter gene was inactive at all lovastatin concentrations tested. Thus lovastatin reverses the effect of fusion of the carboxy terminus of RAS2 a transcriptional activator. We presume that this is due to inhibition of the sterol biosynthetic pathway and consequent depletion of isopropenyl substrates required for farnesylation.

A more precise dose-response of reporter gene activation in YT6::171 containing YCp15Gal112FS to lovastatin concentrations in the range 100 nM to 100 μM was obtained using the CPRG form of the β-galactosidase assay. This dose-response is displayed in FIG. 3B. A continuous reproducible increase in reporter gene induction is observed as the lovastatin concentration is increased.

To obtain further evidence that the RAS2derived sequence in Gal112FS is acting as a farnesylation signal, we also constructed a vector which expresses the activator Gal112NF. Gal112NF is identical to Gal112FS except that the cysteine four residues from the carboxy terminus has been replaced with an alanine. This alteration to the carboxy terminal sequence should destroy the farnesylation signal. Unlike Gal112FS, we found that this activator was as strong as the parental activator Gal112. Increasing concentrations of lovastatin did not induce reporter gene expression activity, but rather caused the level of reporter gene activity to decrease in a manner that closely paralleled the inhibition of growth. These results suggest that, as expected, Gal112NF is neither farnesylated nor membrane associated.

Conclusions

We have shown that fusion of a farnesylation-dependent membrane association signal to a transcriptional activator results in inhibition of the ability of this protein to activate transcription. We have shown that lovastatin can be used to restore the activating ability of this protein. Thus we have used lovastatin to induce expression of a reporter gene. We believe that the mechanism of this induction is via inhibition of farnesylation-dependent membrane association of a chimaeric transcriptional activator. The S. cerevisiae yeast strain described containing the activator Gal112FS readily allows a simple assay for compounds capable of inhibiting farnesylation and farnesylation-dependent membrane association. Using the β-galactosidase assay described, this assay is amenable to use in high throughput screens to identify such compounds, though we advise that if such compounds are also cytotoxic, they may not be detected such a screen.

EXAMPLE 2

Inhibition of membrane association of a transcriptional activator in COS-1 cells by the HMG-CoA reductase inhibitor lovastatin In this example we show that, in a transient transfection in mammalian cells, (i) fusion a membrane association signal to a transcriptional activator causes that protein to become inactive, (ii) that this chimaeric transcriptional activator displays a mobility in gels consistent with lipid modification and (iii) that application o the HMG-CoA reductase inhibitor lovastatin restores the correct mobility of the protein and restores its ability to activate transcription.

COS-1 cells were used as an experimental system. Mammalian cells do not contain any DNA binding proteins with the specificity of the S. cerevisiae protein GAL4. However, GAL4 derivatives which function as transcriptional activators in S. cerevisiae will function in mammalian cells if GAL4 binding sites are placed near the start site or gene transcription (21) To study the function in mammalian cells of the chimaeric activators generated in Example 1, we transferred the genes encoding Gal112FS and Gal112NF into mammalian expression vectors. These constructs were cotransfected into COS-1 cells with a reporter gene consisting of a promoter containing five GAL4 binding sites driving transcription of a β-galactosidase reporter gene.

Materials and methods

Plasmids

The mammalian expression vector pECE72 was created by cloning the insert of pECE (26) as a Pvu II. Bam HI fragment into the backbone of the pUC-based vector pSP72 (Promega) cleaved with PvuII and Bgl II. The vector pECE72 contains the SV40 late region enhancer/promoter followed by a polylinker and the SV40 poly (A) addition site. DNA cloned into the polylinker of this plasmid is expressed at high levels in mammalian cells, particularly cells such as the monkey line COS-1 which amplify the plasmid by replication. Plasmid pECE-FS was obtained by cloning the 0.6 kb Hind III-Spe I fragment of YCp15G112FS into pECE72 cleaved with Hind III and Xba I. pECE-FS expresses the chimaeric transcription factor Gal112FS from the SV40 promoter/enhancer. Plasmid pECE-NF was obtained by cloning the 0.6 kb Hind III. Spe I fragment of YCp15G112NF into pECE72 cleaved with Hind III and Xba I. pECE-NF expresses the chimaeric transcriptional activator Gal112NF from the SV40 promoter/enhancer.

The reporter gene plasmid pG5βGal was constructed in the following way. A 0.1 kb DNA fragment containing 5 consensus GAL4 binding sites was obtained by PCR from the CAT-based reporter plasmid pG5EC (27) using the following oligonucleotides:

CCATGCTTAAGCGCCAAGC (SEQ ID NO:8) and
ATACCCTCTAGAGTCGAC (SEQ ID NO: 9)

This fragment was cleaved with Afl II and Xba I and cloned into the plasmid pVIP-GAL cleaved with Spe I and Afl II. pVIP-GAL. pVIP-GAL (M. Needham/Zeneca Pharmaceuticals) was derived from pGSE1417 (28) and pSVGal (Pharmacia) and is a mammalian expression plasmid containing the E. coli β-galactosidase gene driven by a minimal β-globin promoter. The GAL4 sites were inserted immediately upstream of this promoter to make pGβGal.

Cell culture and transfection

COS-1 cells were maintained in DMEM plus 10% foetal calf serum supplemented with 50 µg/ml penicillin/streptomycin and 2 mM L-glutamine. Calcium chloride transfections were performed essentially as described (25). For each individual transfection, the procedure was as follows. One day prior to transfection $1.5 \times 10^6$ cells were seeded into 75 cm$^2$ flask and incubated overnight at 37 C. One hour prior to transfection fresh media was added. Calcuim chloride precipitates were made with 60 µg per plate of the test plasmids together with 15 µg of pRSVhGH (M. Needham/ Zeneca Pharmaceuticals; as a control for levels of transfection. The precipitate was added to the cells and cells incubated for seven hours at 37 C. followed by a 60 second 15% glycerol shock. Fresh media was added and the cells were allowed to recover for 24 hours. After 24 hours fresh media was added to the flasks. Some flasks also received 1 µM Lovastatin (Merox and Co.) After a further 24 hours the cells were trypsinised, washed twice in phosphate buffered saline and pellet finally resuspended in 300 µl of water. For β-galactosidase assays, $1.25 \times 10^5$ cells were diluted to 200 µl and dispensed into a microtitre well. 50 µl of 5×Z buffer (see Example 1) and CPRG (to a final concentration of 1 mM) and SDS (to a final concentration of 0.1% were added to start the reaction. The rate of reaction was measured as the rate of change in OD570. For Western blots, cell extracts were prepared by freeze-thawing the transfected cells three times. Protein concentration estimated using a protein assay kit (Pierce). Growth hormone assays were performed using a Hybritech kit. Aliquots of cell extract were electrophoresed through 10% polyacrylamide/SDS gels and electroblotted onto nitrocellulose filters. Gal4 derivatives were detected using a 1:500 dilution of GAL4 polyclonal antibody (M. Ptashne. Harvard) and visualised using 1:1000 dilution of a goat anti-rabbit alkaline phosphatase antibody, detected using a NBT/BCIP kit (from Biorad).

Results

We first examined the transcriptional activity of the proteins Gal112FS and Gal112NF in mammalian cells. COS-1 cells were contransfected with the reporter gene plasmid pG5βGal and the expression constructs encoding Gal112FS and Gal112NF. The transfected cells were incubated in the presence or absence of lovastatin. After 24 hours the cells were assayed for β-galactosidase activity. The results are displayed in FIG. 5. COS-1 cells contain an endogenous β-galactosidase activity in the absence of the reporter gene (lanes 1 and 2). Transfection of the reporter gene increases this activity 1.5–2 fold (lanes 3 and 4 ), showing that the reporter gene plasmid pG5βGal is transcribed at a basal level in the absence of any GAL4-based activators. Lovastatin does not increase this basal level; instead it reduces it slightly. Contransfection of the plasmid expressing Gal112NF with the reporter gene resulted in a high level of reporter gene activity (lane 5). This is consistent with the results obtained in Example 1, where Gal112NF was demonstrated to be a strong transcriptional activator. This activator is predicted to be non-lipid modified and consistent with this, lovastatin does not affect its activity (lane 6). Contransfection of the plasmid containing Gal112FS with the reporter gene resulted in a small increase in reporter gene activity compared to reporter gene alone (compare lanes 3 and 7). However, incubation of this transfection with lovastatin resulted in a substantial induction of reporter gene activity (compare lanes 7 and 8). Subtracting respectively the basal levels due to reporter gene alone (lanes 3 and 4), this amounts to an induction of the activity of Gal112FS by lovastatin of 5.8 fold.

Farnesylation and palmitoylation of ras proteins leads to an increase in their electrophoretic mobility in SDS-polyacrylamide gels (ref. 29). We used Western blotting to analyse the mobility of Gal112NF and Gal112FS in the presence and absence of lovastatin. Plasmids pECE-NF and pECE-FS were transfected into COS-1 cells. After incubation in the presence or absence of lovastatin, protein was prepared from the transfected cells and electrophoresed through an SDS-polyacrylamide gel. This was blotted onto a nitrocellulose membrane and probed with anti-Gal4 antibodies. FIG. 6 shows a schematic representation of the resulting Western blot. Lanes 6 and 7 are control lanes which show the result of mock transfections. No protein are detected by Gal4 antibodies in either lane. Lanes 4 and 5 show Gal112NF with and without lovastatin. Gal112FS and Gal112NF are predicted to be about 31 kdal; a band of approximate size 33 kdal is detected in lanes 4 and 5. L ovastatin. no effect on the mobility of this band, implying that Gal112NF is not modified by any intermediate on the sterol biosynthetic pathway. By contrast, lanes 2 and 3 show Gal112FS in the absence and presence of lovastatin respectively. Gal112FS migrates ahead of Gal112NF, despite containing the same number of amino acids in its primary structure. The large mobility difference is consistent with lipid modification (29). In the presence of lovastatin, Gal112FS migrates with the same mobility as Gal112NF. These results from Gal112FS is modified by an intermediate on the sterol biosynthetic pathway, and that lovastatin inhibits this modification.

Discussion

In this example we show that the activator Gal112FS behaves in the same fashion in a mammalian cell line (COS-1) as in S. cerevisiae. Gal112FS has a low activity which can be induced by lovastatin. The control activator Gal112NF is strongly active and its activity is unaffected by lovastatian, again as observed in S. cerevisiae. The mobilities of the proteins as examined by Western blotting are consistent with Gal112FS being lipid-modified. These results demonstrate that activation of reporter gene expression correlates with restoration of normal electrophoretic mobility. With reference to the work of Hancock et. al. (5) we conclude that activation of reporter gene expression results from inhibition of farnesylation. In ras proteins, farnesylation is a requirement for subsequent palmitoylation, proteolytic cleavage and methylation. Therefore the inhibition of farnesylation would result in complete inhibition of lipid modification. These modifications are required for membrane association of ras proteins. A chimaeric protein in which these modification are inhibited should not be associated with a membrane Therefore these results imply that the lovastatin-induced activation of reporter gene expression we observe in both mammalian (COS-1) and yeast (S. cerevisiae) cells is due to the production of a chimaeric activator which is not membrane associated and is therefore able to bind to activate a reporter gene.

We note that the high background of β-galactosidase activity in COS-1 cells and the transient nature of the assay described would not favour the use of mammalian cells as an assay system to detect novel inhibitors of membrane association processes. However, it would be possible to construct stable cell lines containing integrated copies of both Gal112FS and a Gal4-responsive reporter gene. Such a cell line could be conveniently used in high throughput screening.

References:
1. Chow et al., (1992) Curr. Opinion Cell Biol. 61, 355–386.
2. Gibbs (1991), Cell 65, 1–4.
3. Towler et al., (1988) Ann. Rev. Biochem. 57, 69–99.
4. Clarke, (1992) Ann. Rev. Biochem. 61, 355–386.
5. Hancock et al., (1991) EMBO J. 10, 4033–4039.
6. Pellman et al., (1985) Nature 314, 374–377.
7. Durinio et al., (1992) Proc. Natl. Acad. Sci. USA 89, 4129–4133.
8. Brown et al., (1992) Proc. Natl. Acad. Sci. USA 89, 8318–8316.
9. Resh and Ling, (1990) Nature 346, 84–86.
10. Finegold et al., (1990) Science 249, 165–169.
11. Himmelfarb et al., (1990) Cell 63, 1299–1309.
12. Sadowski and Ptashne, (1989) Nuc. Acids Res. 17, 7539.
13. Colicelli et al., (1989) Proc. Natl. Acad. Sci. USA. 86, 3599–3603.
14. Sikorski and Hieter, (1989) Genetics 122, 19–27.
15. Ruden et al., (1991) Nature 350, 250–252.
16. Schafer et al., (1989) Science 380, 379–385.
17. Laughon and Gesteland (1984) Mol. Cell Biol. 4, 260–267.
18. Powers et al., (1984) Cell 36, 607–612.
19. Ito et al., (1983) J. Bacteriol. 153, 163–168.
20. Repko and Maltese (1989) J. Biol. Chem. 264, 9945–9.
21. Ptashne (1988) Nature 335, 683–689.
22. Lenardo and Baltimore (1989) Cell 58, 227–229.
23. Harrison (1991) Nature 353, 715–719.
24. Seabra et al., (1992) Cell 70, 1049–1057.
25. Ausabel et al., (1990) Current Protocols in Molecular Biology Wiley;
26. Ellis et al., (1986) Cell 45, 721–731.
27. Sadowski et al., (1992) Gene 118, 137–141.
28. Needham et al., (1992) Nuc. Acids Res. 20, 997–1003.
29. Hancock et al., (1989) Cell 57, 1167–1177.

I claim:

1. A method of for the identifying a compounds which modulates protein/cell membrane association which method comprises contacting a test compound with a cell, having (i) a cell membrane, (ii) a heterologous protein comprising a reporter sequence and a recognition sequence for cell membrane association, wherein the reporter sequence comprises a transcriptional activator and the recognition sequence directs lipid modification of the heterologous protein, and (iii) a reporter system which is acted upon by the reporter sequence such that there is a measurable change in cell phenotype upon modulation of protein/cell membrane association by the test compound, and detecting any change in cell phenotype, thereby identifying the test compound as a compound which modulates protein/cell membrane association by any change in cell phenotype.

2. The method as claimed in claim 1 wherein the recognition sequence for membrane association is a signal for farnesylation, geranylgeranylation myristoylation, endopeptidase cleavage, carboxy terminus methylation, palmitoylation, or any combination thereof.

3. The method as claimed in claim 1 wherein said compound which modulates protein/cell membrane association is an inhibitor of farnesylation, geranylgeranylation, or myristoylation dependent events.

4. The method as claimed in claim 1 wherein said compound which modulates protein/cell membrane association is an inhibitor of lipid modification of protein.

5. The method as claimed in claim 1 wherein said compound which modulates protein/cell membrane association is an inhibitor of lipid biosynthesis.

6. The method as claimed in claim 1 wherein said compound which modulates protein/cell membrane association is an inhibitor of membrane association of ras proteins.

7. The method as claimed in claim 1 wherein said compound which modulates protein/cell membrane association is obtained from a collection of chemical compounds, natural products and/or broths.

8. The heterologous protein/reporter system of claim 1 which includes a heterologous protein comprising a transcriptional activator and a recognition sequence for cell membrane association, and wherein in the absence of cell membrane association the transcriptional activator activates transcription of a gene encoding a further transcriptional activator, which further transcriptional activator activates transcription of a reporter gene, expression of which leads to a measurable phenotype.

9. The method of claim 1 in which the reporter system includes a heterologous protein comprising a transcriptional activator and a recognition sequence for cell membrane association, and wherein in the absence of cell membrane association the transcriptional activator activates transcription of a gene encoding a further transcriptional activator, which further transcriptional activator activates transcription of a reporter gene, expression of which leads to a measurable phenotype.

10. A cell having (i) a cell membrane, (ii) at least two heterologous proteins, wherein each heterologous protein comprises a transcriptional activator and a recognition sequence for cell membrane association, and (iii) at least two reporter systems, wherein each reporter system is acted upon by at least one of the heterologous proteins such that there is a measurable change in cell phenotype upon modulation of protein/cell membrane association by a test compound.

11. A cell, having (i) a cell membrane, (ii) at least two heterologous proteins, wherein each heterologous protein comprises a transcription activator and a recognition sequence for cell membrane association, (iii) at least two promoter/gene transcription systems wherein each promoter/gene transcription system is acted upon by at least one of the heterologous proteins, such that gene transcription is activated by a compound which inhibits association of the heterologous protein and the cell membrane.

12. A method for identifying a mutant cell defective in protein/cell membrane association which method comprises treating one or more cells as claimed in any one of claims 10 and 11 with one or more mutagenic agents and detecting a cell which is mutated by reference to a change in cell membrane association of the heterologous protein.

13. A method for inducing gene expression which method comprises applying a known inhibitor of cell membrane association to a cell to induce expression of a promoter/gene transcription system, wherein the cell has (i) a cell membrane, (ii) a heterologous protein comprising a transcription activator and a recognition sequence for cell membrane association, (iii) a promoter/gene transcription system which is acted upon by the transcription activator such that gene transcription is activated by a compound which inhibits association of the heterologous protein and the cell membrane.

14. A method for the identification of recognition sequences for cell membrane association which method comprises constructing a population of cells, each having (i) a cell membrane, (ii) a different heterologous protein comprising a reporter sequence and a putative recognition sequence for cell membrane association, wherein the reporter sequence comprises a transcriptional activator and the putative recognition sequence directs lipid modification of the heterologous protein, and (iii) a reporter system which is acted upon by the reporter sequence such that there is a measurable change in cell phenotype upon modulation of protein/cell membrane association;

modulating protein/cell membrane association; and detecting cells in the population with a functional recognition sequence by the change in cell phenotype.

15. Yeast strain *Saccharomyces cerevisiae* YT6::171 comprising the plasmid YCp15Gal112 FS.

* * * * *